US00PP24949P3

(12) United States Plant Patent
Weber

(10) Patent No.: US PP24,949 P3
(45) Date of Patent: Oct. 7, 2014

(54) RASPBERRY PLANT NAMED 'CRIMSON NIGHT'

(50) Latin Name: ***Rubus idaeus* L.**
Varietal Denomination: Crimson Night

(71) Applicant: Cornell University, Ithaca, NY (US)

(72) Inventor: Courtney A. Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 84 days.

(21) Appl. No.: 13/694,090

(22) Filed: Oct. 30, 2012

(65) Prior Publication Data

US 2014/0123350 P1 May 1, 2014

(51) Int. Cl.
*A01H 5/00* (2006.01)

(52) U.S. Cl.
USPC ..... Plt./204

(58) Field of Classification Search
USPC ..... Plt./204
See application file for complete search history.

(56) References Cited

PUBLICATIONS

"Berry Different: Growers Turn To New Cornell Raspberries for Better Flavor, Disease-Resistance And A Colorful Fall Crop," Dec. 7, 2012, Retrieved from the web on Feb. 10, 2013, <http://www.blogs.cornell.edu/stationnews/2012/12/07/berry-different-growers-turn-to-new-cornell-raspberries-for-better-flavor-disease-resistance-and-a-colorful-fall-crop/>, pp. 1-2.

"'Crimson Night' Raspberries," Retrieved from web on Feb. 10, 2013, <http://www.cctec.cornell.edu/events/celebration12/Crimson%20Night.pdf>, p. 1.

"Dark Red Raspberry 'Crimson Night,'" Retrieved from web on Feb. 27, 2013, <http://cornell.flintbox.com/public/project/21015>, pp. 1-2.

Frazer, K., "Growers License New Raspberries," Retrieved from web on Feb. 10, 2013, <blogs.cornell.edu/fruit/2012/12/05/growers-license-new-raspberries/>, pp. 1-2.

Garris, A. "Cornell Releases Two New Raspberry Varieties," Cornell ChronicleOnline, Apr. 30, 2012, Retrieved from web on Feb. 10, 2013, <http:www.news.cornell.edu/stories/April12/Raspberries.html>, pp. 1-2.

Garris, A. "Cornell Releases Two New Raspberry Varieties," Cornell Chronicle, May 4, 2012, p. 1, vol. 43, No. 33.

"Nursery Guide for Berry & Small Fruit Crops," Retrieved from web on Feb. 10, 2013, <http:/www.fruit.cornell.edu/berry/nuseries/raspberries.html>, pp. 1-3.

*Primary Examiner* — Annette Para
(74) *Attorney, Agent, or Firm* — MacMillan, Sobanski & Todd, LLC

(57) ABSTRACT

This invention relates to a new and distinct primocane bearing red raspberry plant designated as 'Crimson Night' primarily adapted to growing conditions of west central New York and other regions of similar climate. The new plant is primarily characterized by highly pigmented canes, conical fruit that is longer than broad, late mid-season primocane production and dark greyed purple fruit color.

4 Drawing Sheets

Genus and species: *Rubus idaeus* L.
Variety denomination: 'Crimson Night'.

BACKGROUND AND SUMMARY OF THE INVENTION

I. Field & Utility Summary

This invention relates to a new and distinct primocane bearing red raspberry plant designated as 'Crimson Night'. The new plant is primarily characterized by highly pigmented canes, conical fruit that is longer than broad, late mid-season primocane production and dark greyed purple fruit color.

Raspberry plant 'Crimson Night' is primarily adapted to the climate and growing conditions of west central New York and other regions of similar temperate climate. This climate allows for the development of sturdy primocanes fruiting in the late mid-fall season from the middle of September to late October. 'Crimson Night' benefits from the use of protective structures such as plastic hoop houses or high tunnels, which allow for optimal cane growth and the complete harvest of the fall crop when the risk of frost is prevalent.

II. Cultivation Summary

The new and distinct red raspberry originated from a hand-pollinated cross of the Cornell selection NY270 (maternal—unpatented) and Cornell selection NY357 (paternal—unpatented).

III. Comparisons

The following traits have been repeatedly observed and are determined to be unique characteristics of 'Crimson Night', which in combination distinguish this raspberry plant as a new and distinct plant:

1. late mid-fall fruit harvest on primocanes;
2. highly pigmented canes;
3. thick sturdy canes;
4. dark greyed purple, glossy fruit; and
5. heavy leaf pigmentation late in the season when temperatures become cool.

'Crimson Night' bears dark, greyed-eyed purple, glossy, large, conical fruit when ripe. 'Crimson Night' fruits on mid-fall primocanes. The canes of 'Crimson Night' are deep red/greyed purple, sturdy, have no waxy coating and a moderate number of short, stout spines.

Maternal parent plant NY270 bears red, large, conical fruit on less sturdy primocanes. The canes of NY270 collapse easily due to large internal cavities.

Paternal parent plant NY357 bears dark red/purple, moderately-sized, round fruit on floricanes. The primocanes of NY357 are pigmented and do not produce fruit.

Unrelated raspberry variety 'Heritage' (unpatented) bears red, small, round fruit on primocanes, seven days earlier than 'Crimson Night'. The canes of 'Heritage' 'Heritage' are sturdy, upright, heavily greyed-red pigmented, and have many stout spines.

Unrelated raspberry variety 'Caroline' (U.S. Plant Pat. No. 10,412) bears dark red, dull, moderate to large, and broad conical (slightly broader than long) fruit. The canes of 'Caroline' are variably pigmented red purple to greyed yellow, with few short spines and a waxy coating.

'Caroline' and 'Heritage', 'Crimson Night' differs by the following combination of characteristics described in Table 1. Color terminology is based on The Royal Horticultural Society colour chart (2001 edition).

TABLE 1

| Characteristic | 'Crimson Night' | 'Caroline' (PP10,412) | 'Heritage' |
|---|---|---|---|
| 1. Mature primocane color | Greyed-purple 187A | Red purple 59B Greyed-yellow 160A | Greyed-red 180B |
| 2. Fruit shape | Conical | Broad conical | Round |
| 3. Fruit length (mm) | 21 | 18 | 15 |
| 4. Fruit width (mm) | 17 | 19 | 14 |
| 5. Fruit length × width ratio | 1.2 | 0.9 | 1.1 |
| 6. Mean fruit weight | 2.8 g | 2.5 g | 1.9 |
| 7. Maximum fruit weight | 4.2 | 3.8 | 3.0 |
| 8. Mature fruit color | Greyed purple 187B | Red 45A | Red 53A |
| 9. Canes per plant | 25 | 31 | 29 |
| 10. Fruiting laterals/ primocane | 13 | 14 | 18 |
| 11. Leaflet number | 3 | 5 | Primarily 3 with up to 10% 5 |

IV. Breeding History

The new and distinct red raspberry originated from a hand-pollinated cross of the Cornell selection NY270 (unpatented) and Cornell selection NY357 (unpatented). This cross was made and the resulting seedling grown in Geneva, N.Y. The seedling was selected from a controlled breeding plot in 2003 and was designated NY03-56 for testing. NY03-56 was subsequently designated 'Crimson Night'.

V. Asexual Reproduction

Raspberry plant 'Crimson Night' has been asexually propagated by dormant canes in Geneva, N.Y. since 2004 and was established in tissue culture in Geneva, N.Y. in 2008.

VI. Stability

Asexual propagation as described has demonstrated that the combination of traits that characterize this plant are fixed and remain true to type through successive generations.

BRIEF DESCRIPTION OF THE FIGURES

The accompanying color photographs show typical specimens of the new plant at various stages of development as nearly true as it is possible to make in color reproductions. Color in the photographs may differ slightly from the color value cited in the detailed botanical description, which accurately describes the color of 'Crimson Night'. The photographs of canes and fruit were taken in Geneva, N.Y. in the second year of harvesting fruit.

DETAILED BOTANICAL DESCRIPTION OF THE INVENTION

Figure 1A:
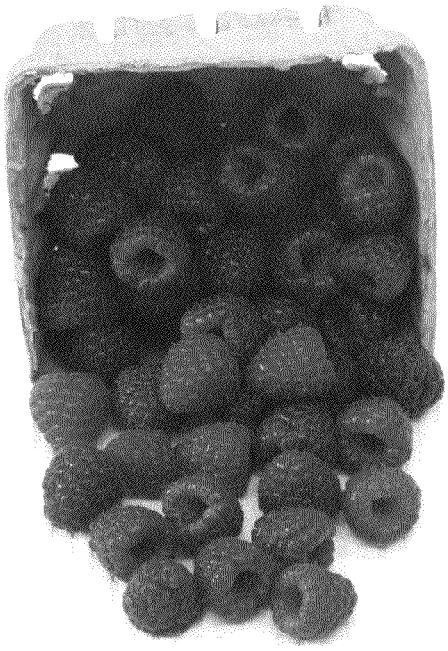
FIG. 1A is a photo of typical fruit shape and size of 'Crimson Night' in a container.
Figure 1B:
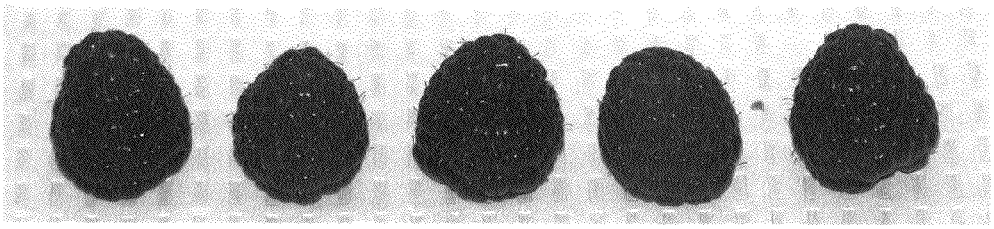
FIG. 1B from a top view.
Figure 1C:
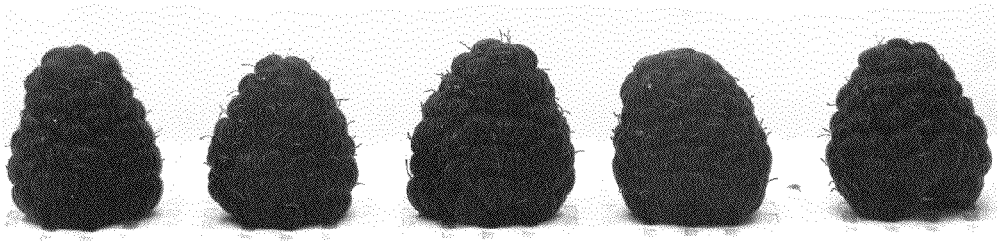
FIG. 1C from a side view.
Figure 2A:
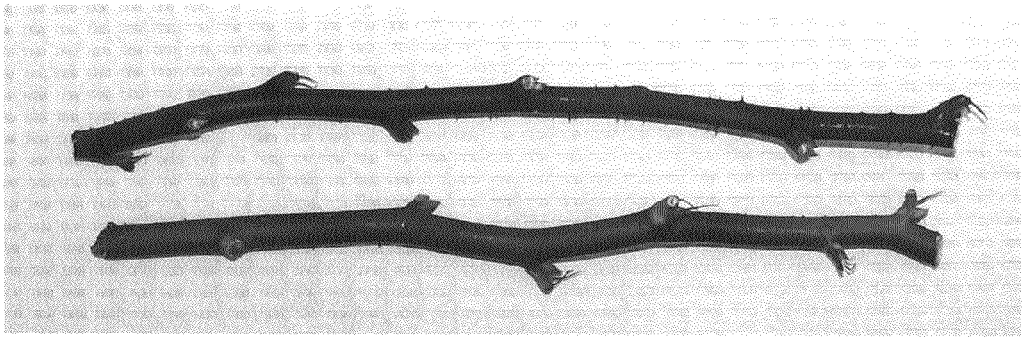
FIG. 2A is a photo of typical primocane pigmentation viewed from two sides of the same cane for 'Crimson Night'.
Figure 2B:
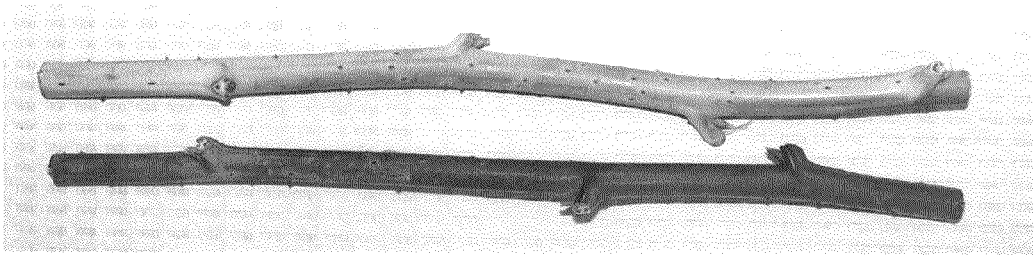
FIG. 2B is a photo of typical primocane pigmentation viewed from two sides of the same cane for 'Caroline'.
Figure 2C:
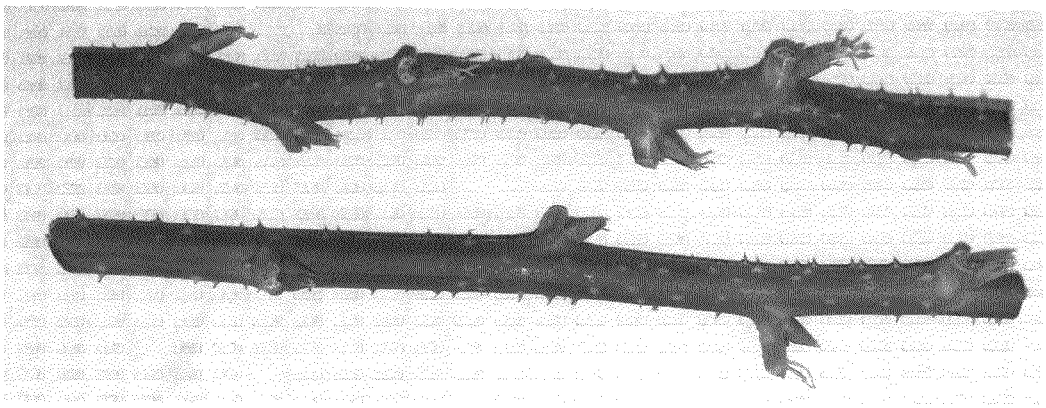
FIG. 2C is a photo of typical primocane pigmentation viewed from two sides of the same cane for 'Heritage'.
Figure 3A:
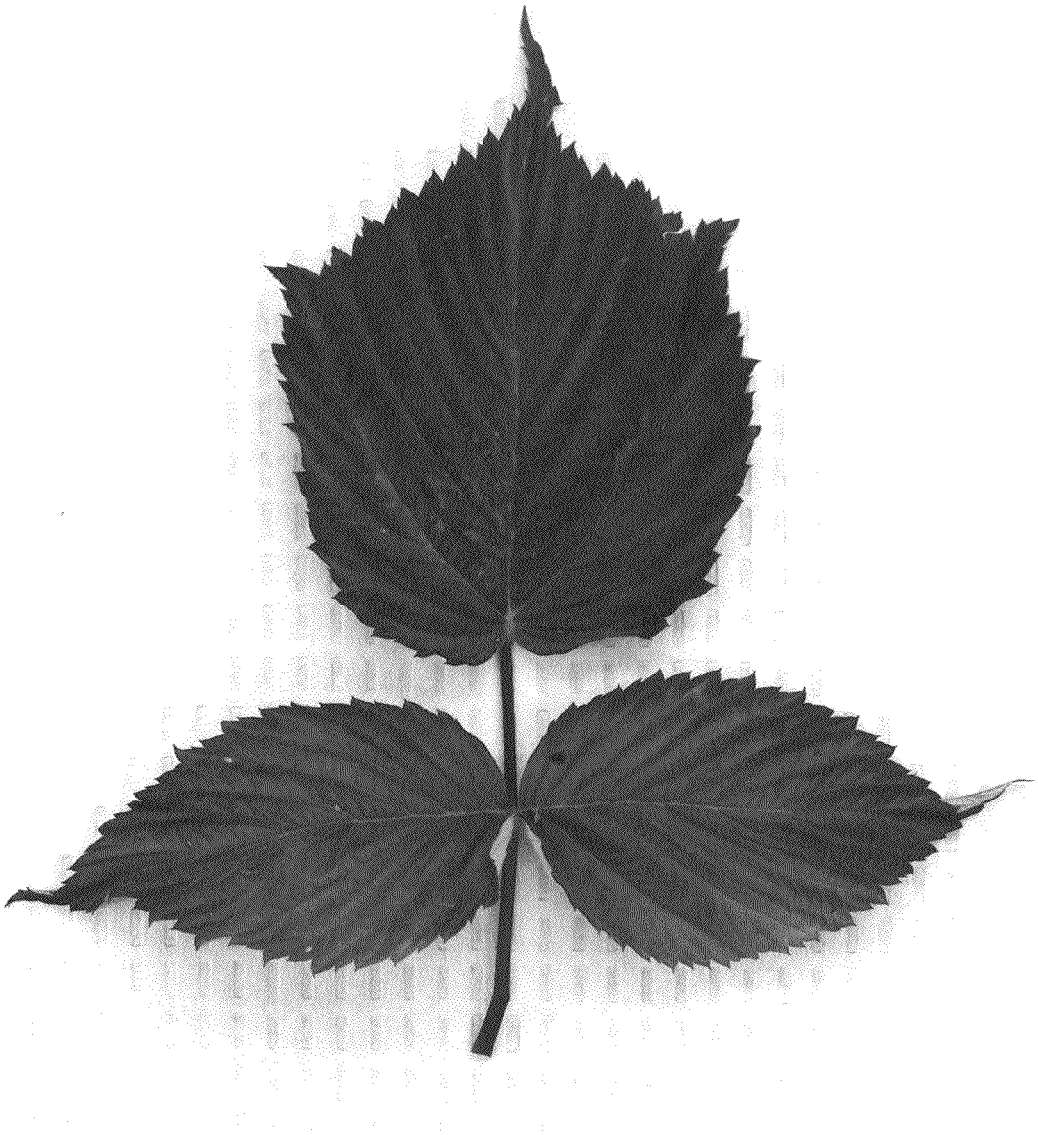
FIG. 3A is a photo of mature leaves nearing senescence showing pigmentation and leaflet number for 'Crimson Night'.
Figure 3B:
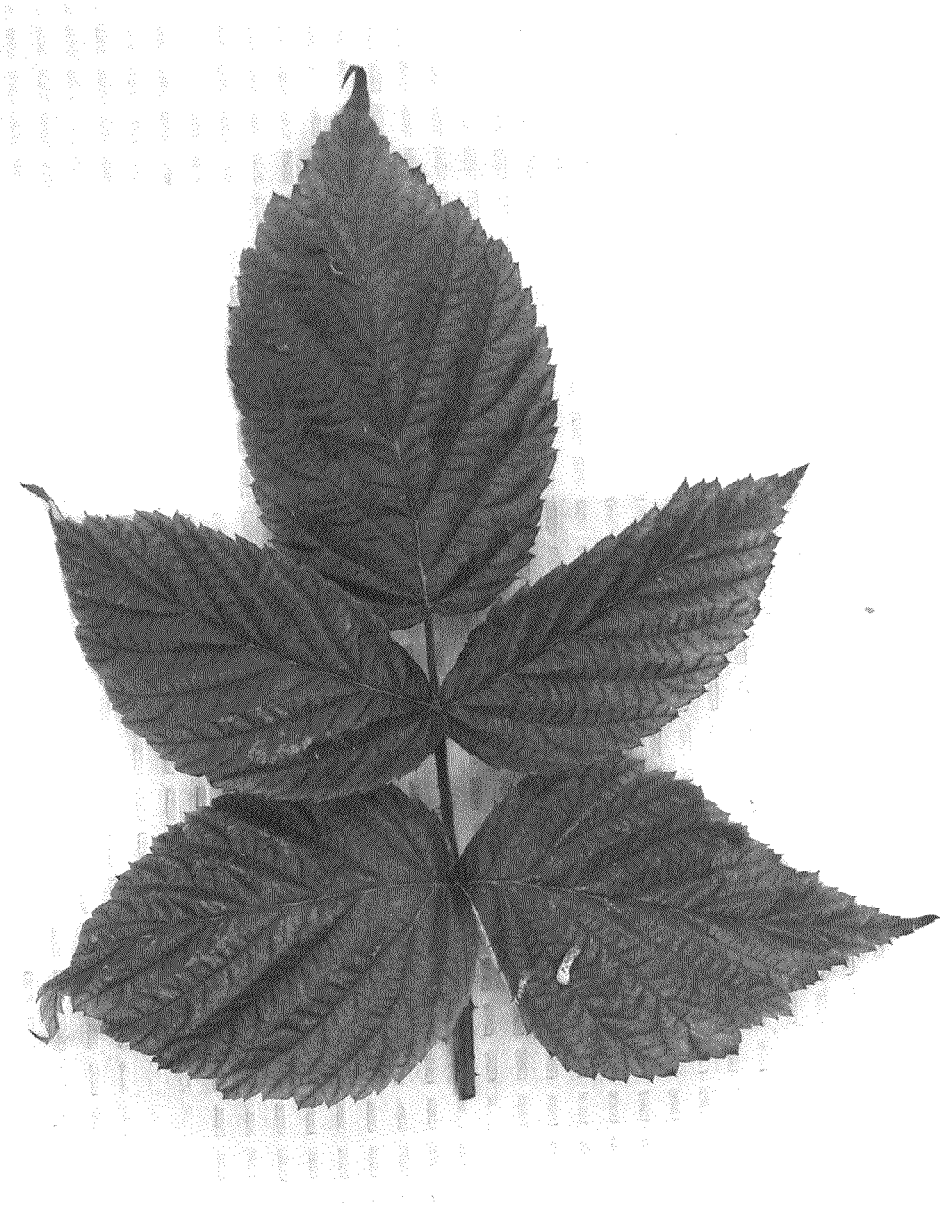
FIG. 3B is a photo of mature leaves nearing senescence showing pigmentation and leaflet number 'Caroline'.

'Crimson Night' has not been observed under all possible environmental conditions and as such the characteristics may vary in detail depending on weather conditions, day length, soil type and location.

The photographs together with the description of the new raspberry 'Crimson Night' are based upon the observations taken during the 2012 growing season in Geneva, N.Y. Measurements were taken on plants grown in a perennial planting in a high tunnel system that was planted in Geneva, N.Y. in 2009 with the canes emerging naturally in late April 2012. Flower measurements and characteristics were taken from secondary flowers and fruit measurements from secondary fruit. Mean measurements of fruit size were taken on 10 fruit samples throughout the season. Measurements of flower and fruit parts are means of 10 fruit samples. Cane measurements taken within the center third of the cane unless otherwise noted.

Primocanes:

*Cane color.*—Greyed-purple group 187A.
*Spines.*—Present.
*Cane length.*—1.3 m-1.6 m; mean 1.5 m.
*Cane diameter.*—7-10 mm; mean 9 mm.
*Number of fruiting lateral branches.*—11-15; mean 13.
*Maximum fruiting lateral length.*—29.5 cm.
*Pubescence.*—None.

Spines:

*Density.*—High at base, moderate at middle third.
*Form.*—Stout.
*Length.*—Mean 1.5 mm.
*Apex.*—Curved downward.
*Color.*—Greyed-purple 187A on mature canes.

Leaves:

*Type.*—Compound; typically 3 leaflets.
*Mature leaflet color.*—Upper surface Green 137A; lower surface Greyed-green 194B.
*Arrangement.*—Free.
*Terminal leaflet length.*—8.5-13.5 cm; mean 10.9 cm.
*Terminal leaflet width.*—5.5-11.3 cm; mean 8.4 cm.
*Terminal leaflet length to width ratio.*—1.3.
*Basal leaflet length.*—5.3-10.0 cm; mean 8.3 cm.
*Basal leaflet width.*—3.8-6.5 cm; mean 5.9 cm.
*Basal leaflet length to width ratio.*—1.4.
*Leaflet shape.*—Ovate.
*Terminal leaflet tip.*—Cuspidate.
*Basal leaflet tip.*—Auriculate.
*Leaflet margins.*—Doubly serrate.
*Terminal leaflet number of serrations.*—102 mean.
*Basal leaf attachment.*—Flush.
*Leaflet overlap.*—None.
*Petiole length.*—5.7 cm.

*Petiole width.*—2.7 mm.
*Petiole spines.*—Present.
*Petiole spine apex.*—Slight curve toward stem.
*Petiole color.*—Greyed purple 187A.

Stipules:
*Quantity per leaf.*—2.
*Shape.*—Straight and erect.
*Length.*—5-7 mm; mean 6.1 mm.
*Color.*—Greyed purple 187A.

Flowers:
*Diameter.*—0.9-1.1 cm; mean 1.1 cm.
*Bud shape.*—Conical.
*Fragrance.*—None.
*Petals number.*—Typically 5.
*Petal shape.*—Obovate.
*Petal length.*—6-7 mm; mean 6.2 mm.
*Petal width.*—2-3 mm; mean 2.7 mm.
*Petal length to width ratio.*—2.4.
*Petal color.*—White 155C.
*Sepal number.*—Typically 5.
*Sepal length.*—6-8 mm; mean 6.6 mm.
*Sepal color.*—Upper surface Greyed-green 193A; lower surface Green 143C.
*Mean stigma number.*—85.
*Stigma color.*—White 155B.
*Mean stamen number.*—110.
*Anther color.*—White 155A.
*Anther filament color.*—White 155D.
*Stamen height.*—Below stigmatic surface.

Fruit:
*Shape.*—Broad conic.
*Fruit length.*—1.9-2.4 cm; mean 2.1 cm.
*Fruit width.*—1.6-2.0 cm; mean 1.7 cm.
*Fruit length to width ratio.*—1.2.
*Weight.*—1.8-4.2 g; mean 2.8 g.
*Number of drupelets.*—85.
*Color of mature fruit.*—Greyed purple 185B early and later greyed purple 187B.
*Pedicel diameter.*—1 mm.
*Pedicel spines.*—Present; curved back towards cane.
*Adherence to receptacle.*—Moderate.

I claim:

1. A new and distinct raspberry plant as herein described and illustrated.

* * * * *